US009750565B2

(12) United States Patent
Bloom et al.

(10) Patent No.: US 9,750,565 B2
(45) Date of Patent: Sep. 5, 2017

(54) ELECTROSURGICAL BALLOONS

(75) Inventors: Eliot F. Bloom, Hopkinton, NH (US); Vaclav O. Podany, Dover, NH (US); Chad M. Greenlaw, Somersworth, NH (US); Brian M. Conley, South Berwick, ME (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 1239 days.

(21) Appl. No.: 13/250,104

(22) Filed: Sep. 30, 2011

(65) Prior Publication Data

US 2013/0085493 A1    Apr. 4, 2013

(51) Int. Cl.
*A61B 18/14* (2006.01)
*A61B 18/00* (2006.01)
*A61B 18/12* (2006.01)

(52) U.S. Cl.
CPC ...... *A61B 18/1492* (2013.01); *A61B 2018/00255* (2013.01); *A61B 2018/00404* (2013.01); *A61B 2018/00434* (2013.01); *A61B 2018/00511* (2013.01); *A61B 2018/126* (2013.01); *A61B 2018/1472* (2013.01); *A61B 2218/002* (2013.01)

(58) Field of Classification Search
USPC .............................................. 606/41, 48, 50
See application file for complete search history.

(56) References Cited

U.S. PATENT DOCUMENTS

| | | |
|---|---|---|
| 2,888,928 A | 6/1959 | Seiger |
| 3,682,130 A | 8/1972 | Jeffers |
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,244,371 A | 1/1981 | Farin |
| 4,248,224 A | 2/1981 | Jones |
| 4,275,734 A | 6/1981 | Mitchiner |
| 4,276,874 A | 7/1981 | Wolvek et al. |

(Continued)

FOREIGN PATENT DOCUMENTS

| | | |
|---|---|---|
| WO | WO96/04955 A2 | 2/1996 |
| WO | WO2010/141417 | 12/2010 |

OTHER PUBLICATIONS

Salameh, F., et al., "An animal model study to clarify and investigate endoscopic tissue coagulation by using new monopolar device," *Gastrointestinal Endoscopy* 59:107-112, American Society for Gastrointestinal Endoscopy (2004).

(Continued)

*Primary Examiner* — Paula J Stice
(74) *Attorney, Agent, or Firm* — Christopher & Weisberg, P.A.

(57) ABSTRACT

An electrosurgical balloon includes an inflatable balloon body formed of a non-conductive substrate material. One or more electrodes are disposed on an exterior surface of the balloon body. The electrodes can include a pair of bipolar electrodes, and the balloon body can have at least one fluid outlet hole configured to provide fluid to the pair of bipolar electrodes. A second inflatable balloon body can be disposed inside the first inflatable balloon body. The electrosurgical balloon can be incorporated into a catheter assembly, in which the electrosurgical balloon is a balloon electrode tip at a distal end of a catheter.

3 Claims, 9 Drawing Sheets

(56) References Cited

U.S. PATENT DOCUMENTS

| | | |
|---|---|---|
| 4,278,090 A | 7/1981 | van Gerven |
| 4,321,931 A | 3/1982 | Hon |
| 4,342,218 A | 8/1982 | Fox |
| 4,355,642 A | 10/1982 | Alferness |
| 4,377,168 A | 3/1983 | Rzasa et al. |
| 4,381,007 A | 4/1983 | Doss |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,671,274 A | 6/1987 | Scrochenko |
| 4,736,749 A | 4/1988 | Lundback |
| 4,779,611 A | 10/1988 | Grooters et al. |
| 4,802,475 A | 2/1989 | Weshahy |
| 4,919,129 A | 4/1990 | Weber et al. |
| 4,931,047 A | 6/1990 | Broadwin et al. |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,047,028 A | 9/1991 | Qian |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Midler |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowle |
| 5,330,521 A | 7/1994 | Cohen |
| 5,334,181 A | 8/1994 | Rubinsky et al. |
| 5,334,193 A | 8/1994 | Nardella |
| 5,336,220 A | 8/1994 | Ryan et al. |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,383,874 A | 1/1995 | Jackson et al. |
| 5,385,148 A | 1/1995 | Lesh et al. |
| 5,395,312 A | 3/1995 | Desai |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,401,272 A | 3/1995 | Perkins |
| 5,403,309 A | 4/1995 | Coleman et al. |
| 5,403,311 A | 4/1995 | Abele et al. |
| 5,405,376 A | 4/1995 | Mulier et al. |
| 5,409,483 A | 4/1995 | Campbell et al. |
| 5,417,709 A | 5/1995 | Slater |
| 5,423,807 A | 6/1995 | Milder |
| 5,423,811 A | 6/1995 | Imran et al. |
| 5,427,119 A | 6/1995 | Swartz et al. |
| 5,431,168 A | 7/1995 | Webster, Jr. |
| 5,431,649 A | 7/1995 | Mulier et al. |
| 5,433,708 A | 7/1995 | Nichols et al. |
| 5,435,308 A | 7/1995 | Gallup et al. |
| 5,437,651 A | 8/1995 | Todd et al. |
| 5,441,503 A | 8/1995 | Considine et al. |
| 5,443,463 A | 8/1995 | Stern et al. |
| 5,443,470 A | 8/1995 | Stern et al. |
| 5,445,638 A | 8/1995 | Rydell et al. |
| 5,450,843 A | 9/1995 | Moll et al. |
| 5,452,582 A | 9/1995 | Longsworth |
| 5,452,733 A | 9/1995 | Sterman et al. |
| 5,460,629 A | 10/1995 | Shlain et al. |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,490,819 A | 2/1996 | Nicholas et al. |
| 5,496,271 A | 3/1996 | Burton et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,700 A | 4/1996 | Leone |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,562 A | 7/1996 | Giter |
| 5,540,679 A | 7/1996 | Fram et al. |
| 5,542,916 A | 8/1996 | Hirsch et al. |
| 5,542,945 A | 8/1996 | Fritzsch |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,556,397 A | 9/1996 | Long et al. |
| 5,558,671 A | 9/1996 | Yates |
| 5,560,362 A | 10/1996 | Silwa, Jr. et al. |
| 5,562,702 A | 10/1996 | Huitema et al. |
| 5,562,720 A | 10/1996 | Stern et al. |
| 5,569,241 A | 10/1996 | Edwards |
| 5,569,243 A | 10/1996 | Kortenbach et al. |
| 5,571,088 A | 11/1996 | Lennox et al. |
| 5,571,215 A | 11/1996 | Sterman et al. |
| 5,573,424 A | 11/1996 | Poppe |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,588,432 A | 12/1996 | Crowley |
| 5,590,657 A | 1/1997 | Cain et al. |
| 5,595,183 A | 1/1997 | Swanson et al. |
| 5,599,346 A | 2/1997 | Edwards et al. |
| 5,605,539 A | 2/1997 | Buelna et al. |
| 5,607,422 A | 3/1997 | Smeets et al. |
| 5,607,462 A | 3/1997 | Imran |
| 5,617,854 A | 4/1997 | Munsif |
| 5,630,837 A | 5/1997 | Crowley |
| 5,637,090 A | 6/1997 | McGee et al. |
| 5,643,197 A | 7/1997 | Brucker et al. |
| 5,647,869 A | 7/1997 | Goble et al. |
| 5,656,029 A | 8/1997 | Imran et al. |
| 5,658,278 A | 8/1997 | Imran et al. |
| 5,671,747 A | 9/1997 | Connor |
| 5,673,695 A | 10/1997 | McGee et al. |
| 5,676,662 A | 10/1997 | Fleischhacker et al. |
| 5,676,692 A | 10/1997 | Sanghvi et al. |
| 5,676,693 A | 10/1997 | Lafontaine |
| 5,678,550 A | 10/1997 | Bassen et al. |
| 5,680,860 A | 10/1997 | Imran |
| 5,681,278 A | 10/1997 | Igo et al. |
| 5,681,294 A | 10/1997 | Osborne et al. |
| 5,681,308 A | 10/1997 | Edwards et al. |
| 5,687,723 A | 11/1997 | Avitall |
| 5,687,737 A | 11/1997 | Branham et al. |
| 5,688,267 A | 11/1997 | Panescu et al. |
| 5,690,611 A | 11/1997 | Swartz et al. |
| 5,697,536 A | 12/1997 | Eggers et al. |
| 5,697,882 A | 12/1997 | Eggers et al. |
| 5,697,925 A | 12/1997 | Taylor |
| 5,697,927 A | 12/1997 | Imran et al. |
| 5,697,928 A | 12/1997 | Walcott et al. |
| 5,713,942 A | 2/1998 | Stern |
| 5,716,389 A | 2/1998 | Walinsky et al. |
| 5,718,241 A | 2/1998 | Ben-Haim et al. |

(56) References Cited

U.S. PATENT DOCUMENTS

| | | |
|---|---|---|
| 5,718,701 A | 2/1998 | Shai et al. |
| 5,720,775 A | 2/1998 | Larnard |
| 5,722,402 A | 3/1998 | Swanson et al. |
| 5,730,074 A | 3/1998 | Peter |
| 5,730,127 A | 3/1998 | Avitall |
| 5,730,704 A | 3/1998 | Avitall |
| 5,733,280 A | 3/1998 | Avitall |
| 5,735,280 A | 4/1998 | Sherman et al. |
| 5,735,290 A | 4/1998 | Sterman et al. |
| 5,743,903 A | 4/1998 | Stern et al. |
| 5,746,224 A | 5/1998 | Edwards |
| 5,755,760 A | 5/1998 | Maguire et al. |
| 5,766,167 A | 6/1998 | Eggers et al. |
| 5,769,846 A | 6/1998 | Edwards et al. |
| 5,782,828 A | 7/1998 | Chen et al. |
| 5,785,706 A | 7/1998 | Bednarek |
| 5,788,636 A | 8/1998 | Curley |
| 5,792,140 A | 8/1998 | Tu et al. |
| 5,797,905 A | 8/1998 | Fleischman et al. |
| 5,797,960 A | 8/1998 | Stevens et al. |
| 5,800,428 A | 9/1998 | Nelson et al. |
| 5,800,482 A | 9/1998 | Pomeranz et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,844,349 A | 12/1998 | Oakley et al. |
| 5,846,187 A | 12/1998 | Wells et al. |
| 5,846,191 A | 12/1998 | Wells et al. |
| 5,849,028 A | 12/1998 | Chen |
| 5,861,021 A | 1/1999 | Thome et al. |
| 5,871,523 A | 2/1999 | Fleischman et al. |
| 5,871,525 A | 2/1999 | Edwards et al. |
| 5,873,845 A | 2/1999 | Cline et al. |
| 5,873,855 A | 2/1999 | Eggers et al. |
| 5,876,399 A | 3/1999 | Chia et al. |
| 5,879,295 A | 3/1999 | Li et al. |
| 5,879,296 A | 3/1999 | Ockuly et al. |
| 5,879,348 A | 3/1999 | Owens et al. |
| 5,881,732 A | 3/1999 | Sung et al. |
| 5,882,346 A | 3/1999 | Pomeranz et al. |
| 5,885,278 A | 3/1999 | Fleischman |
| 5,891,142 A | 4/1999 | Eggers et al. |
| 5,893,848 A | 4/1999 | Negus et al. |
| 5,895,355 A | 4/1999 | Schaer |
| 5,895,417 A | 4/1999 | Pomeranz et al. |
| 5,897,553 A | 4/1999 | Mulier et al. |
| 5,897,554 A | 4/1999 | Chia et al. |
| 5,899,898 A | 5/1999 | Arless et al. |
| 5,899,899 A | 5/1999 | Arless et al. |
| 5,902,289 A | 5/1999 | Swartz et al. |
| 5,904,711 A | 5/1999 | Flom et al. |
| 5,906,580 A | 5/1999 | Kline-Schoder et al. |
| 5,906,587 A | 5/1999 | Zimmon |
| 5,906,606 A | 5/1999 | Chee et al. |
| 5,908,029 A | 6/1999 | Knudson et al. |
| 5,913,854 A | 6/1999 | Maguire et al. |
| 5,916,213 A | 6/1999 | Haissaguerre et al. |
| 5,916,214 A | 6/1999 | Cosio et al. |
| 5,921,924 A | 7/1999 | Avitall |
| 5,921,982 A | 7/1999 | Lesh et al. |
| 5,925,045 A | 7/1999 | Reimels et al. |
| 5,927,284 A | 7/1999 | Borst et al. |
| 5,928,191 A | 7/1999 | Houser et al. |
| 5,931,810 A | 8/1999 | Grabek |
| 5,931,848 A | 8/1999 | Saadat |
| 5,935,123 A | 8/1999 | Edwards et al. |
| 5,944,715 A | 8/1999 | Goble et al. |
| 5,954,661 A | 9/1999 | Greenspon et al. |
| 5,957,919 A | 9/1999 | Laufer |
| 5,971,980 A | 10/1999 | Sherman |
| 5,971,983 A | 10/1999 | Lesh |
| 5,980,516 A | 11/1999 | Mulier et al. |
| 5,989,248 A | 11/1999 | Tu et al. |
| 5,993,412 A | 11/1999 | Deily et al. |
| 5,993,447 A | 11/1999 | Blewett et al. |
| 6,004,269 A | 12/1999 | Crowley et al. |
| 6,004,316 A | 12/1999 | Laufer |
| 6,004,319 A | 12/1999 | Goble et al. |
| 6,007,499 A | 12/1999 | Martin et al. |
| 6,010,500 A | 1/2000 | Sherman et al. |
| 6,012,457 A | 1/2000 | Lesh |
| 6,015,391 A | 1/2000 | Rishton et al. |
| 6,016,811 A | 1/2000 | Knopp et al. |
| 6,018,676 A | 1/2000 | Davis et al. |
| 6,019,757 A | 2/2000 | Scheldrup |
| 6,024,733 A | 2/2000 | Eggers et al. |
| 6,030,381 A | 2/2000 | Jones et al. |
| 6,036,687 A | 3/2000 | Laufer et al. |
| 6,042,556 A | 3/2000 | Beach et al. |
| 6,048,333 A | 4/2000 | Lennox et al. |
| 6,056,744 A | 5/2000 | Edwards |
| 6,056,745 A | 5/2000 | Panescu et al. |
| 6,056,746 A | 5/2000 | Goble |
| 6,056,747 A | 5/2000 | Saadat et al. |
| 6,063,081 A | 5/2000 | Mulier |
| 6,066,139 A | 5/2000 | Ryan et al. |
| 6,068,653 A | 5/2000 | LaFontaine |
| 6,071,279 A | 6/2000 | Whayne et al. |
| 6,083,237 A | 7/2000 | Huitema et al. |
| 6,086,585 A | 7/2000 | Hovda et al. |
| 6,088,894 A | 7/2000 | Oakley |
| 6,091,995 A * | 7/2000 | Ingle et al. .................. 607/138 |
| 6,096,037 A | 8/2000 | Mulier |
| 6,113,592 A | 9/2000 | Taylor |
| 6,113,596 A | 9/2000 | Hooven et al. |
| 6,117,101 A | 9/2000 | Diederich et al. |
| 6,120,496 A | 9/2000 | Whayne et al. |
| 6,141,576 A | 10/2000 | Littmann et al. |
| 6,142,993 A | 11/2000 | Whayne et al. |
| 6,142,994 A | 11/2000 | Swanson et al. |
| 6,149,620 A | 11/2000 | Baker et al. |
| 6,149,646 A | 11/2000 | West et al. |
| 6,152,920 A | 11/2000 | Thompson et al. |
| 6,161,543 A | 12/2000 | Cox et al. |
| 6,165,174 A | 12/2000 | Jacobs et al. |
| 6,190,384 B1 | 2/2001 | Ouchi |
| 6,193,716 B1 | 2/2001 | Shannon, Jr. |
| 6,210,406 B1 | 4/2001 | Webster |
| 6,210,410 B1 | 4/2001 | Farin et al. |
| 6,210,411 B1 | 4/2001 | Hofmann et al. |
| 6,212,426 B1 | 4/2001 | Swanson |
| 6,216,704 B1 | 4/2001 | Ingle et al. |
| 6,217,528 B1 | 4/2001 | Koblish et al. |
| 6,217,576 B1 | 4/2001 | Tu et al. |
| 6,224,592 B1 | 5/2001 | Eggers et al. |
| 6,231,518 B1 | 5/2001 | Grabek et al. |
| 6,231,591 B1 | 5/2001 | Desai |
| 6,235,020 B1 | 5/2001 | Cheng et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,387 B1 | 5/2001 | Miller, III |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,110 B1 | 6/2001 | Wampler |
| 6,251,128 B1 | 6/2001 | Knopp et al. |
| 6,258,087 B1 | 7/2001 | Edwards et al. |
| 6,264,650 B1 | 7/2001 | Hovda et al. |
| 6,266,551 B1 | 7/2001 | Osadchy et al. |
| 6,270,471 B1 | 8/2001 | Hechel et al. |
| 6,283,988 B1 | 9/2001 | Laufer et al. |
| 6,283,989 B1 * | 9/2001 | Laufer et al. .................. 607/96 |
| 6,293,943 B1 | 9/2001 | Panescu et al. |
| 6,296,619 B1 | 10/2001 | Brisken et al. |
| 6,299,633 B1 | 10/2001 | Laufer |
| 6,302,880 B1 | 10/2001 | Schaer |
| 6,311,692 B1 | 11/2001 | Vaska et al. |

(56) References Cited

U.S. PATENT DOCUMENTS

| | | |
|---|---|---|
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,322,559 B1 | 11/2001 | Daulton et al. |
| 6,325,797 B1 | 12/2001 | Stewart et al. |
| 6,328,735 B1 | 12/2001 | Curley et al. |
| 6,328,736 B1 | 12/2001 | Mulier |
| 6,332,881 B1 | 12/2001 | Carner et al. |
| 6,352,533 B1 | 3/2002 | Ellman et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,371,956 B1 | 4/2002 | Wilson et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,416,509 B1 | 7/2002 | Goble et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier et al. |
| 6,477,396 B1 | 11/2002 | Mest et al. |
| 6,478,793 B1 | 11/2002 | Cosman et al. |
| 6,484,727 B1 | 11/2002 | Vaska et al. |
| 6,488,678 B2 | 12/2002 | Sherman |
| 6,488,680 B1 | 12/2002 | Francischelli |
| 6,497,704 B2 | 12/2002 | Ein-Gal |
| 6,502,575 B1 | 1/2003 | Jacobs et al. |
| 6,508,815 B1 | 1/2003 | Strul et al. |
| 6,514,250 B1 | 2/2003 | Jahns |
| 6,517,536 B2 | 2/2003 | Hooven et al. |
| 6,527,767 B2 | 3/2003 | Wang et al. |
| 6,537,248 B2 | 3/2003 | Mulier |
| 6,558,382 B2 | 5/2003 | Jahns |
| 6,558,385 B1 | 5/2003 | McClurken et al. |
| 6,575,969 B1 | 6/2003 | Rittman, III et al. |
| 6,579,288 B1 | 6/2003 | Swanson et al. |
| 6,584,360 B2 | 6/2003 | Francischelli |
| 6,585,732 B2 | 7/2003 | Mulier |
| 6,602,248 B1 | 8/2003 | Sharps et al. |
| 6,603,988 B2 | 8/2003 | Dowlatshahi |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,635,034 B1 | 10/2003 | Cosmescu |
| 6,645,199 B1 | 11/2003 | Jenkins et al. |
| 6,645,202 B1 | 11/2003 | Pless et al. |
| 6,648,883 B2 | 11/2003 | Francischelli |
| 6,656,174 B1 | 12/2003 | Hegde et al. |
| 6,656,175 B2 | 12/2003 | Francischelli |
| 6,663,627 B2 | 12/2003 | Francischelli |
| 6,666,862 B2 | 12/2003 | Jain et al. |
| 6,679,882 B1 | 1/2004 | Kornerup |
| 6,682,501 B1 | 1/2004 | Nelson |
| 6,689,131 B2 | 2/2004 | McClurken |
| 6,692,450 B1 | 2/2004 | Coleman |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,766,202 B2 | 7/2004 | Underwood et al. |
| 6,766,817 B2 | 7/2004 | da Silva |
| 6,773,433 B2 | 8/2004 | Stewart et al. |
| 6,775,575 B2 | 8/2004 | Bommannan et al. |
| 6,776,780 B2 | 8/2004 | Mulier |
| 6,786,906 B1 | 9/2004 | Cobb |
| 6,807,968 B2 | 10/2004 | Francischelli |
| 6,827,713 B2 | 12/2004 | Bek et al. |
| 6,827,715 B2 | 12/2004 | Francischelli |
| 6,832,996 B2 | 12/2004 | Woloszko et al. |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,915,806 B2 | 7/2005 | Pacek et al. |
| 6,916,318 B2 | 7/2005 | Francischelli |
| 6,918,404 B2 | 7/2005 | Dias da Silva |
| 6,936,046 B2 | 8/2005 | Hissong |
| 6,942,661 B2 | 9/2005 | Swanson |
| 6,949,097 B2 | 9/2005 | Stewart et al. |
| 6,949,098 B2 | 9/2005 | Mulier |
| 6,953,461 B2 | 10/2005 | McClurken et al. |
| 6,960,205 B2 | 11/2005 | Jahns |
| 6,962,589 B2 | 11/2005 | Mulier |
| 7,066,586 B2 | 6/2006 | da Silva |
| 7,104,990 B2 | 9/2006 | Jenkins et al. |
| 7,156,845 B2 | 1/2007 | Mulier et al. |
| 7,166,106 B2 | 1/2007 | Bartel et al. |
| 7,207,471 B2 | 4/2007 | Heinrich et al. |
| 7,232,440 B2 | 6/2007 | Dumbauld et al. |
| 7,247,155 B2 | 7/2007 | Hoey et al. |
| 7,252,665 B2* | 8/2007 | Starkebaum et al. ......... 606/41 |
| 7,261,711 B2 | 8/2007 | Mulier et al. |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,455,669 B2 | 11/2008 | Swanson |
| 7,537,595 B2 | 5/2009 | McClurken |
| 7,571,729 B2 | 8/2009 | Saadat et al. |
| 7,604,635 B2 | 10/2009 | McClurken et al. |
| 7,608,072 B2 | 10/2009 | Swanson |
| 7,645,277 B2 | 1/2010 | McClurken et al. |
| 7,651,494 B2 | 1/2010 | McClurken et al. |
| 7,691,050 B2 | 4/2010 | Gellman et al. |
| 7,736,361 B2 | 6/2010 | Palanker |
| 7,811,282 B2 | 10/2010 | McClurken |
| 7,815,634 B2 | 10/2010 | McClurken et al. |
| 7,819,861 B2 | 10/2010 | Auge et al. |
| 7,909,820 B2 | 3/2011 | Lipson |
| 7,942,872 B2 | 5/2011 | Ein-Gal |
| 7,976,544 B2 | 7/2011 | McClurken et al. |
| 7,993,337 B2 | 8/2011 | Lesh |
| 7,997,278 B2 | 8/2011 | Utley et al. |
| 7,998,140 B2 | 8/2011 | McClurken et al. |
| 8,034,071 B2 | 10/2011 | Scribner et al. |
| 8,038,670 B2 | 10/2011 | McClurken |
| 8,048,070 B2 | 11/2011 | O'Brien et al. |
| 8,083,736 B2 | 12/2011 | McClurken et al. |
| 8,105,323 B2 | 1/2012 | Buysse et al. |
| 8,172,828 B2 | 5/2012 | Chang et al. |
| 8,177,783 B2 | 5/2012 | Davison et al. |
| 8,216,233 B2 | 7/2012 | McClurken |
| 8,348,946 B2 | 1/2013 | McClurken |
| 8,361,068 B2 | 1/2013 | McClurken |
| 8,388,642 B2 | 3/2013 | Muni et al. |
| 2002/0045892 A1* | 4/2002 | Kramer .................... 606/21 |
| 2002/0049483 A1 | 4/2002 | Knowlton |
| 2002/0062131 A1 | 5/2002 | Gallo, Sr. |
| 2002/0082634 A1 | 6/2002 | Kammerer et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |

(56) References Cited

U.S. PATENT DOCUMENTS

| | | |
|---|---|---|
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0059966 A1 | 3/2005 | McClurken et al. |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2007/0049920 A1 | 3/2007 | McClurken et al. |
| 2007/0093808 A1 | 4/2007 | Mulier et al. |
| 2007/0118114 A1 | 5/2007 | Miller et al. |
| 2007/0149965 A1 | 6/2007 | Gallo, Jr. et al. |
| 2007/0208332 A1 | 9/2007 | Mulier et al. |
| 2008/0004656 A1 | 1/2008 | Livneh |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0103494 A1 | 5/2008 | Rioux |
| 2008/0207028 A1 | 8/2008 | Schutz |
| 2008/0221567 A1 | 9/2008 | Sixto et al. |
| 2008/0262489 A1 | 10/2008 | Steinke |
| 2009/0054892 A1* | 2/2009 | Rioux et al. .................. 606/41 |
| 2009/0177192 A1 | 7/2009 | Rioux et al. |
| 2009/0264879 A1 | 10/2009 | McClurken et al. |
| 2009/0270856 A1 | 10/2009 | Saadat et al. |
| 2009/0306655 A1 | 12/2009 | Stangenes et al. |
| 2010/0069904 A1 | 3/2010 | Cunningham |
| 2010/0100095 A1 | 4/2010 | McClurken et al. |
| 2010/0160906 A1 | 6/2010 | Jarrard |
| 2010/0168743 A1 | 7/2010 | Stone et al. |
| 2010/0204560 A1 | 8/2010 | Salahieh et al. |
| 2010/0241178 A1 | 9/2010 | Tilson et al. |
| 2010/0312259 A1 | 12/2010 | Houser et al. |
| 2010/0331883 A1 | 12/2010 | Schmitz et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0095461 A1 | 4/2012 | Herscher et al. |
| 2012/0101496 A1 | 4/2012 | Mcclurken et al. |
| 2012/0116397 A1 | 5/2012 | Rencher et al. |
| 2012/0143293 A1 | 6/2012 | Mauch et al. |
| 2012/0150165 A1 | 6/2012 | Conley et al. |
| 2012/0157989 A1 | 6/2012 | Stone et al. |
| 2012/0184983 A1 | 7/2012 | Chang et al. |
| 2012/0191084 A1 | 7/2012 | Davison et al. |
| 2012/0253343 A1 | 10/2012 | McClurken et al. |

OTHER PUBLICATIONS

Palanker, D. V., et al., "Electrosurgery with Cellular Precision," *IEEE Transactions on Biomedical Engineering* 55:838-841, IEEE (2008).

Barrx Brochure, "HALO Systems: Advanced Ablation Technology for Treating Barrett's Esophagus," Barrx Medical Incorporated (2008), 8 pages.

PCT International Search Report and Written Opinion dated Mar. 22, 2013.

* cited by examiner

ELECTROSURGICAL BALLOONS

BACKGROUND OF THE INVENTION

Field of the Invention

The present invention relates to medical devices, particularly to an electrosurgical balloon having one or more electrodes disposed on an exterior surface of the balloon, and a bipolar electrode configuration in which a pair of bipolar electrodes are disposed on an exterior surface of the balloon.

Background Art

Medicine is providing ever-increasing demands for devices that can navigate narrow passageways to a desired location within a body so that diagnostic and therapeutic procedures can be performed at that location. Currently, elongated medical devices such as catheters can extend into a body from outside via an access point through various connected passageways to a target location. It is sometimes desirable to perform electrosurgical procedures at the target location.

An electrosurgical procedure involves a medical device having an electrode tip that is electrically energized to perform a procedure such as coagulation, dissection, desiccation and cautery. The electrical energy can be provided in either direct current (DC) form or in alternating current (AC) form. Low frequency electrical energy, including DC, can stimulate muscle and nerves and have potentially undesirable outcomes, such as cardiac arrest, if not properly handled. Higher frequency electrical energy, and in particular electrical energy in the radiofrequency (RF) range (e.g., about 3 kilohertz to about 300 gigahertz), may not stimulate muscle or nerves, and therefore may be better suited to core and coagulate tissue. An electrode tip energized by ultrasonic energy can also be used to perform electrosurgical procedures such as coagulation and tissue ablation.

Modern day elongated medical devices can provide percutaneous access to inner organs and other tissue, and can allow clinicians to navigate to remote and narrow locations within a body. To provide such percutaneous access, these elongated medical devices must meet a variety of requirements such as a desired length, a sufficiently small outer diameter to permit navigation to narrow body passageways, and sufficiently large inner diameter to permit delivery of the required functionality to the remote location. In the case of an elongated medical device having an RF-powered electrode tip, for example, the device can have an inner diameter sufficiently large to transfer the required energy to the electrode tip. To guide the electrode tip to the target site within a body, the elongated medical device including the electrode tip can be deployed into the body through a small trocar. The elongated medical device is advanced in the body to the target site in the body, and the electrode tip is energized at the target site to perform the electrosurgical procedure. An elongated delivery system (e.g., a delivery catheter and/or guidewire) can be used to guide the elongated medical device through the body to the target site.

Electrode tips delivering RF energy can be monopolar or bipolar. A monopolar tip includes one electrode, and a ground pad electrode is located on the patient. Energy applied through the electrode travels through the patient to ground, typically the ground pad. With a bipolar tip, the ground pad electrode located on the patient is eliminated and replaced with a second electrode pole as part of the tip. These active and return electrodes of a bipolar tip are typically positioned close together to ensure that, upon application of electrical energy, current flows directly from the active to the return electrode. Bipolar tips can be advantageous compared to monopolar tips because the return current path only minimally flows through the patient. In bipolar tips, both the active and return electrode are typically exposed so they may both contact tissue, thereby providing a return current path from the active to the return electrode through the tissue. Also, the depth of tissue penetration may be advantageously less with a bipolar tip than with a monopolar tip. Whether monopolar or bipolar, electrode tips made of rigid materials govern the size and shape of the electrode tip that can be deployed through a small trocar and through narrow passageways in the body. The size and shape of the electrode tip can affect the functionality and performance capabilities of the electrode tip at a remote surgical site in the body.

BRIEF SUMMARY

What is needed is an electrode tip that can have a size and shape to achieve desired functionality and performance capabilities at a surgical site, with minimal or no size restrictions arising from the diameter of the elongated medical device, the trocar, and/or the delivery catheter. The present invention satisfies the above needs and provides further related advantages as will be made apparent by the description of the embodiments that follow.

Electrosurgical balloons and catheter assemblies employing electrosurgical balloons as electrode tips are presented. In some embodiments, an electrosurgical balloon includes an inflatable balloon body formed of a non-conductive substrate material, a pair of bipolar electrodes disposed on an exterior surface of the balloon body, and at least one fluid outlet hole in the balloon body. The fluid outlet hole can be configured to provide a conductive fluid from a fluid source to the pair of bipolar electrodes. The pair of bipolar electrodes include a first electrode and a second electrode in a bipolar electrode configuration.

In some embodiments, a catheter assembly includes a catheter and a balloon electrode tip. The catheter includes an elongated body having a distal end portion to which the balloon electrode tip is attached. The balloon electrode tip includes an inflatable balloon body formed of a non-conductive substrate material, a pair of bipolar electrodes disposed on an exterior surface of the balloon body, and at least one fluid outlet hole in the balloon body configured to provide a fluid from a fluid source to the pair of bipolar electrodes.

In some embodiments, a catheter assembly includes a first catheter, a second catheter, and a balloon electrode tip. The first catheter includes a first elongated body having a first distal end portion, and the second catheter includes a second elongated body having a second distal end portion and a lumen. The first catheter is disposed within the lumen. The balloon electrode tip is attached to the first distal end portion, and includes an outer inflatable balloon body formed of a non-conductive substrate material, an inner inflatable balloon body disposed inside the outer inflatable balloon body, and an electrode disposed on an exterior surface of the outer balloon body.

Methods of using a balloon electrode tip to treat tissue are also presented.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention. In the drawings, like reference numbers, letters, or renderings indicate identical or functionally similar elements.

DETAILED DESCRIPTION OF THE INVENTION

Figure 1:
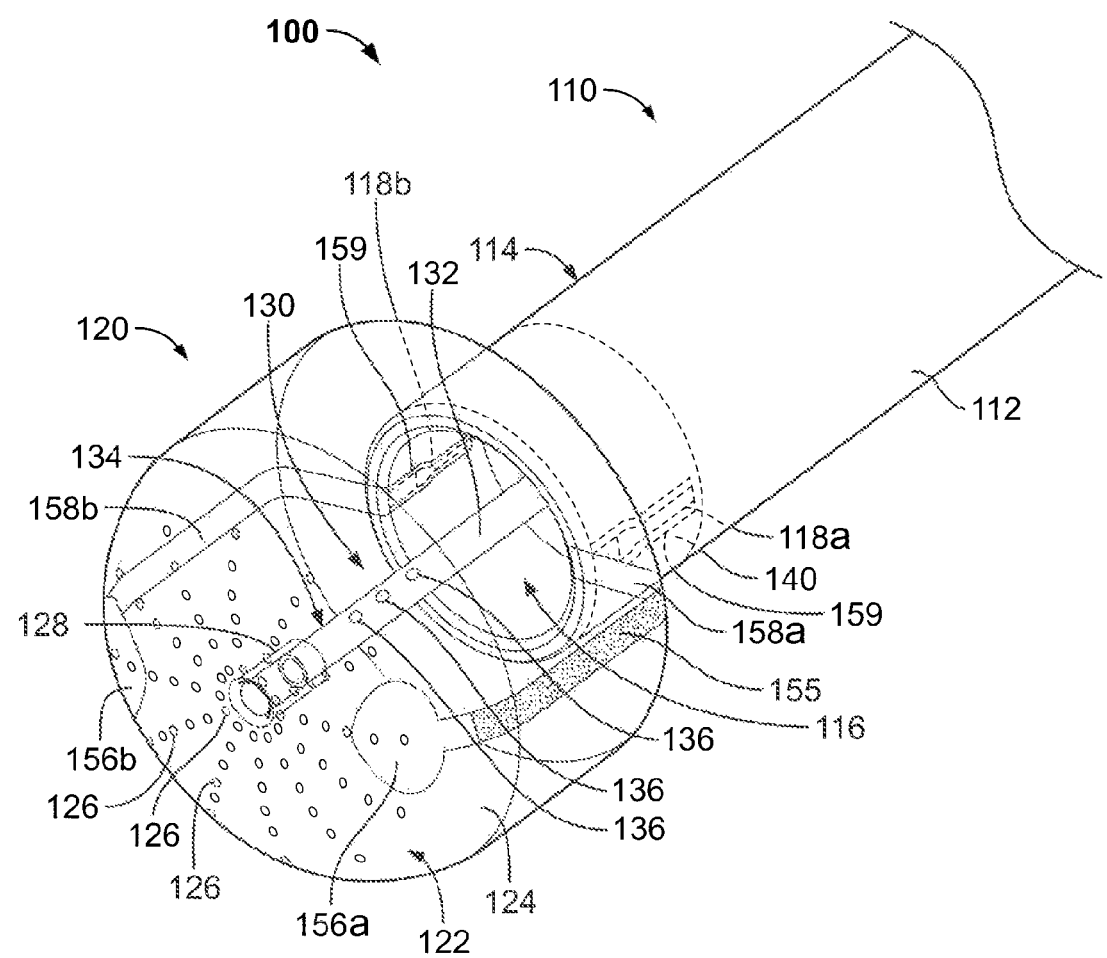
FIG. 1 illustrates a perspective view of a catheter assembly having a balloon electrode tip in an inflated configuration according to an embodiment presented herein.

Unless defined otherwise, all technical and scientific terms used herein have the same meaning as commonly understood by one of ordinary skill in the art to which this invention belongs. In case of conflict, the present application including the definitions will control. Also, unless otherwise required by context, singular terms shall include pluralities and plural terms shall include the singular. All publications, patents and other references mentioned herein are incorporated by reference in their entireties for all purposes.

The term "invention" or "present invention" as used herein is a non-limiting term and is not intended to refer to any single embodiment of the particular invention but encompasses all possible embodiments as described in the application.

According to some embodiments of the present invention, an electrosurgical balloon includes one or more electrodes integrated onto the exterior surface of an expandable balloon (i.e., a balloon that can be expanded by inflation with a gas or liquid). The balloon can formed of a non-conductive substrate material. The electrosurgical balloon can be incorporated into a catheter assembly. The balloon can be disposed at a distal end of an elongated medical device (e.g., a catheter) to provide the catheter with electrosurgical functionality. Catheter lead wire(s) that can be connected to a power source at a proximal end of the catheter are carried by the catheter to the catheter's distal end to connect with the electrode(s).

The one or more electrodes can be formed of any suitable material. For example, the electrode(s) can be a biocompatible conductive wire (such as stainless steel or titanium) adhered to the exterior surface of the balloon, or the electrode(s) can be formed of a conductive ink applied (e.g., by a printing or stamping process) to the surface of the balloon substrate material. The wire or conductive ink electrode(s) on the balloon's surface can include an exposed electrode portion (for tissue treatment at a surgical site) and a lead portion (formed of wire or conductive ink). The electrode lead portion can be soldered to a distal end portion of the catheter lead wire(s). The solder connections and the electrode lead portion can be insulated (e.g., using an insulative material (such as ink or paint that is nonconductive) deposited over a conductive ink electrode, or using an insulative sheath on a wire electrode). The conductive ink for forming an electrode can include ink or paint formed of conductive materials such as, for example, metallic particles (e.g., powdered or flaked silver), carbon, conductive polymers or similar materials. The conductive ink can also include a compliant material that allows dry conductive ink on the balloon to spread with balloon expansion, thereby maintaining the conductive pathway from the catheter lead wire to the electrode lead portion to the exposed electrode portion.

The proximal end of the balloon can be mounted to a rigid ring which is fed into the distal end of the catheter, and the rigid ring can be the site for soldering of the electrode lead portion with the catheter lead wire. The balloon can be made of compliant material (e.g., silicone, latex) or non-compliant material (e.g., PVC, PE, PET). The balloon material can be porous or non-porous with respect to the fluid used for inflation (e.g., saline). The balloon can have a double diameter (with a smaller diameter proximal end and a larger diameter distal end) for stability and to facilitate mounting to the catheter. The balloon can be any configuration or shape (e.g., tubular, spherical) and can be various sizes, allowing the balloon to be designed for a myriad of therapies. The size and shape of the balloon when inflated a given inflation amount can be tailored based on the anatomical site(s) where the balloon is intended to be deployed for an electrosurgical operation, as well as the size of the patient (e.g., sized for adult anatomies (i.e., a comparatively large balloon size) or sized for infant anatomies (i.e., a comparatively small balloon size)).

The electrosurgical balloon can be provided with a monopolar (single) electrode system or a bipolar (double) electrode system. The electrode(s) can be configured to provide an appropriate wattage for the treatment. For example, for bipolar RF treatments in some embodiments, the bipolar electrodes of the electrosurgical balloon can be supplied with RF energy in a range of from about 2 to about 60, from about 10 to about 50, from about 15 to about 45, or from about 10 to about 30 watts. In some embodiments, an electrosurgical procedure is conducted with the bipolar electrodes of the electrosurgical balloon using about 18 watts of RF energy. The level of electrical power used in conjunction with a bipolar system (as well as monopolar system) can be varied and optimized for a particular application, and, if sufficiently high, can generate heat sufficient to dissect, coagulate, or otherwise heat-treat the tissue to which it is applied. This can render the tissue suitable for a variety of surgical procedures, such as, for example, blunt dissection. Exemplary tissue treatment procedures that can employ the balloon electrodes described herein include, for example, dissection and coagulation as mentioned above, as well as blunt dissection with coagulation, spot coagulation, and coagulation of large tissue planes.

The inflation amount of a balloon is adjustable, thereby allowing individualized size adjustments at the surgical site of a particular patient. The inflation amount (measured by the internal pressure (e.g., psi) in the balloon) can be varied to improve the conformability of the balloon to tissue surfaces, even on irregular tissue surfaces. Greater conformability of the balloon to the tissue surface can increase the electrode area in contact with tissue, which may result in reduced treatment times and/or reduced power requirements. Non-compliant balloons can assure a distance between electrodes, and ensure the inflated balloon size and shape is substantially maintained to a predetermined configuration. The inflation amount can also be used to adjust the gap between bipolar electrodes if the balloon is compliant. For RF treatments, variation in the gap between bipolar electrodes can vary the RF application to the tissue. For example, the closer the bipolar electrodes are to each other the more focused the RF energy that is applied to the area between the electrodes, permitting deeper penetration of the RF energy into the tissue in that area. In some embodiments, one or more of the electrode(s) on the balloon surface are configured to deliver ultrasonic therapies. In some embodiments, the electrosurgical balloon is configured to provide both, RF applications and ultrasonic applications.

In some embodiments, a bipolar electrode pair is provided on the exterior surface of the balloon. The electrode pair includes a first electrode (e.g., active electrode) serving as a first pole of a bipolar electrode configuration and a second electrode (e.g., return electrode) serving as a second pole of the bipolar electrode configuration. The electrodes are separated from each other on the balloon's exterior surface, and are insulated from each other by the separation area formed by the non-conductive balloon substrate material. Weeping holes are provided in the balloon substrate material. After delivery to the treatment site in its deflated state, the balloon can be inflated with a fluid. A portion of the fluid can exit through the weeping holes. The weeping holes are specifically positioned in the balloon so as to ensure that fluid exiting the balloon is provided to the pair of electrodes so as to fluidly connect the electrodes together. In some embodiments, the fluid used to inflate the balloon is a conductive fluid (e.g., saline). The weeping holes in the balloon allow the conductive fluid to flow ("weep") to the pair of electrodes. The wept conductive fluid produces an electric coupling to the treatment site by providing a conductive pathway for energy to flow between the pair of electrodes at the treatment site. Moreover, the weeping of fluid can mitigate any thermal expansion of the balloon arising from heat dissipating from the energized electrodes.

The weeping holes can be configured to open to release the conductive fluid only once the balloon has been expanded to a given inflation amount. For example, a complaint (e.g., silicone) balloon can be formed by dipping a mandrel in silicon and curing the silicon, as known to one of skill in the art. The mandrel can be configured to form a balloon having areas of differing thickness. For example, the mandrel can be provided with dimples (or alternatively, bumps), which form corresponding bumps (or alternatively, corresponding dimples) in the balloon that have a greater thickness than the remainder of the balloon. These bumps (or dimples) in the balloon serve as the sites for pin holes, which can be formed in the bumps (or dimples) of the balloon in the deflated configuration. The thickness of the bump (or dimple) to the size of the pin hole is such that the hole is effectively too small for release of the conductive fluid when the balloon is deflated, but opens to form the weeping hole once the balloon is inflated. Alternatively, the balloon can be provided with a uniform thickness (without dimples/bumps) so that the pin holes can be provided anywhere in the balloon. The balloon thickness to the size of the pin hole is such that the pin holes are too small for release of the conductive fluid when the balloon is deflated, but opens to form the weeping holes once the balloon is inflated. Alternatively or in addition to the weeping holes that are configured to open only upon balloon inflation, the balloon may be provided with weeping holes configured to be always open regardless of the state of inflation of the balloon.

In some embodiments, in addition to weeping holes, drug delivery holes can be provided in the balloon for delivery of drugs from a drug source to the treatment site. Thus, both electrosurgical and pharmaceutical-based therapies can be applied to the treatment site using the electrosurgical balloon.

In some embodiments, the electrosurgical balloon can include two balloons: an outer balloon and an inner balloon (see, e.g., catheter assembly 200 described below with references to FIGS. 5-7). The outer balloon can be provided with one or more electrodes on its exterior surface as described above. The inner balloon (disposed inside the chamber of the outer balloon) provides support to the outer balloon. Each of the inner and outer balloons can be made of a compliant or non-compliant material. Each of the inner and outer balloons are inflatable, and each can be inflated with a fluid from a fluid source. When the electrosurgical balloon is deployed (i.e., inflated at the treatment site), the outer balloon can be adjustably inflated with fluid, whereas the inner balloon can always filled with fluid (without adjustment).

In some embodiments, the outer balloon is made of a compliant material, and the inner balloon is made of a non-compliant material. In some embodiments, the outer balloon is made of a non-compliant material, and the inner balloon is made of a compliant material. In some embodiments, both the inner and outer balloons are made of a compliant material, and in other embodiments, both the inner and outer balloons are made of a non-compliant material. The fluid can be a gas (e.g., air) or a liquid (e.g., saline). In some embodiments, the outer balloon is configured to be inflated with a liquid, and the inner balloon is configured to be inflated with a gas. In some embodiments, the outer balloon is provided with a pair of electrodes having a bipolar electrode configuration. In such embodiments, the outer balloon can be selectively inflated with fluid from a fluid source and has weeping holes for dispensing the fluid to the pair of electrodes as earlier described. The inner balloon can be used for support and keeping the electrodes on the outer balloon in place during tissue treatment, while the outer balloon can be controlled to vary the inflation amount and pressure so as to control the amount of fluid that weeps, the surface area contact, and the distance between bipolar electrodes.

In some embodiments, the catheter can be slidably disposed within a lumen of an outer catheter. In some embodiments, the catheter can be fully retracted within the outer catheter so that the deflated balloon can reside in the lumen of the outer catheter until deployed at the treatment site. In some embodiments, the balloon is attached to both the distal end of the inner catheter and the distal end of the outer catheter. When the balloon is inflated, movement of the inner catheter relative to the outer catheter can force the balloon out of or into the lumen of the outer catheter, and the application of such force can change the shape and internal pressure of the balloon. This relative movement of the catheters can be used to control the balloon area in contact with the tissue. The movement can be used to control the amount of fluid that weeps and, for bipolar embodiments, the distance between bipolar electrodes.

In some embodiments, the catheter assembly constituted by the catheter and the electrosurgical balloon (serving as the balloon electrode tip) in its deflated configuration can extend through the lumen of a 2-French or larger catheter. In operation, the catheter assembly (including the inner catheter, the outer catheter if provided, and the electrosurgical balloon) can be delivered through a trocar to a percutaneous treatment site using a delivery system. As an example only and not by way of limitation, a delivery catheter is inserted through the trocar to a specific treatment site. A guidewire is inserted through the delivery catheter to the treatment site. The delivery catheter is removed, and the catheter assembly is advanced along the guidewire to the site. The electrosurgical balloon is extended from the outer catheter (if provided) at the site and inflated. The electrode(s) on the balloon's exterior surface are energized and targeted tissue is contacted with the energized balloon electrode tip. After the electrosurgical procedure is conducted, the guidewire and the catheter assembly are be removed either simultaneously or sequentially in any order.

The electrosurgical balloon according to embodiments presented herein allows increased surface area to be in contact with the targeted tissue beyond the standard 5 mm trocar diameter of typical laparoscopic instruments. Thus, a catheter assembly including the electrosurgical balloon allows delivery of a large electrode system through a small trocar. The electrosurgical balloon can allow electrosurgical procedures to be conducted using an electrode system that has a size and shape to achieve desired functionality and performance capabilities at the surgical site, with minimal or no size restrictions arising from the diameter of the catheter assembly, the trocar, and/or the delivery catheter.

Embodiments of the electrosurgical balloon described herein can be used for many procedures, including percutaneous treatment of aneurysms, treatment of mitral valve regurgitation by tightening the annulus around the mitral valve, treatments in the upper and lower gastrointestinal tract (GI) (including, e.g., bleeding varices, ulcers, caustic poisons, Crohn's disease), diverticulosis, varicose veins, sympathetic nerves (e.g., renal denervation by RF ablation), tumors, gene and stem cell therapies, and other surgical procedures in which treatment can include vessel sealing/coagulation, tissue shrinkage, and/or tissue ablation.

To further illustrate electrosurgical balloons and catheter assemblies disclosed herein, exemplary embodiments will now be described with reference to the Figures. It should be understood that any features of an embodiment disclosed herein can be combined with any features of any other embodiment disclosed herein, without departing from the scope of the present disclosure. Thus, any of the features of the electrosurgical balloons and catheter assemblies described above can be combined with any features of the exemplary embodiments described below with reference to the Figures.

Figure 2:
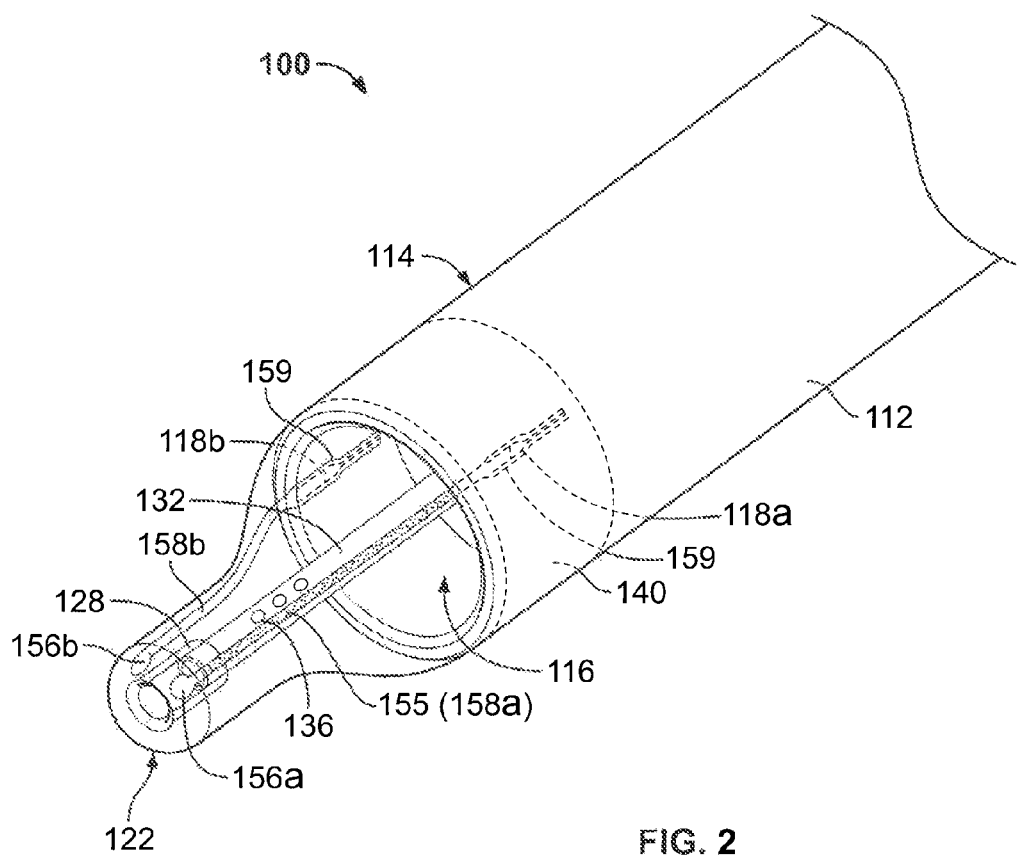
FIG. 2 illustrates a perspective view of the catheter assembly of FIG. 1 having the balloon electrode tip in a deflated configuration according to an embodiment presented herein.

FIGS. 1 and 2 illustrate an exemplary catheter assembly 100 according to an embodiment presented herein. Catheter assembly 100 includes an outer catheter 110, an inner catheter 130, and a balloon electrode tip 120. FIG. 1 illustrates balloon electrode tip 120 in an inflated configuration, and FIG. 2 illustrates tip 120 in a deflated configuration.

Figure 3A:
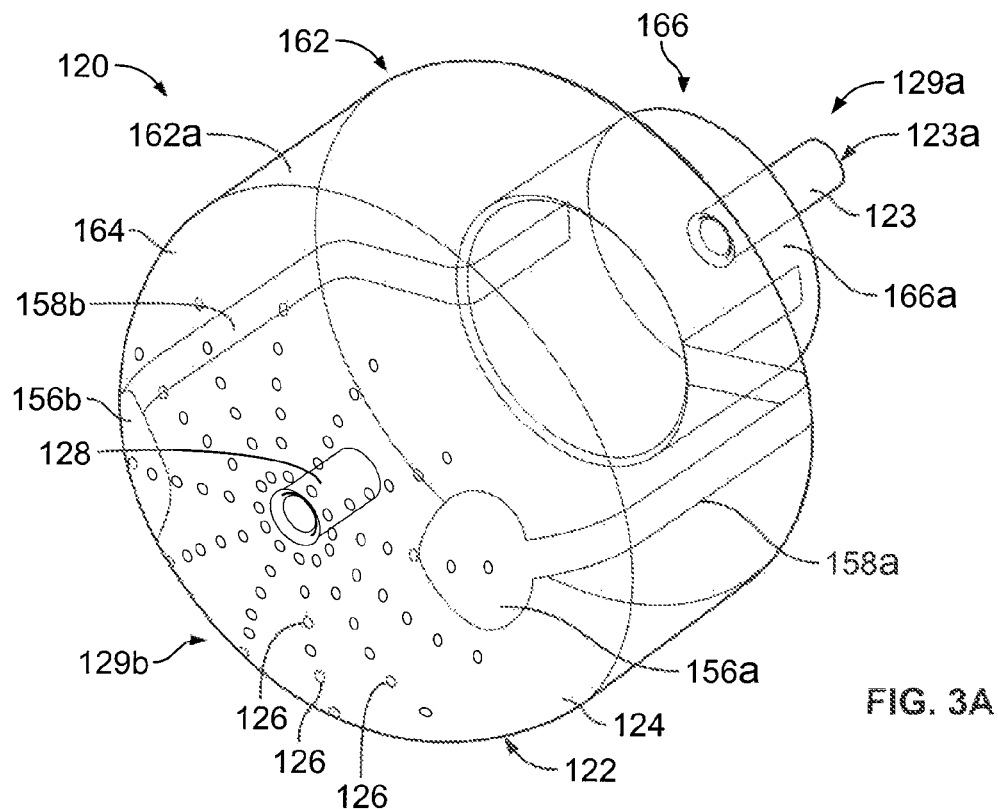
FIG. 3A illustrates a perspective view of the balloon electrode tip of FIG. 1 with electrodes disposed on a distal end of the balloon according to an embodiment presented herein.

Outer catheter 110 has an elongated body 112 with a lumen 116. Lumen 116 can extend from a proximal end portion (not shown) to a distal end portion 114. Inner catheter 130 is disposed within lumen 116 of outer catheter 110. Inner catheter 130 has an elongated body 132 and a distal end portion 134. In some embodiments, balloon electrode tip 120 is attached to distal end portion 134 of inner catheter 130. In some embodiments, balloon electrode tip 120 is also attached to distal end portion 114 of outer catheter 110. FIG. 3A illustrates balloon electrode tip 120 (absent catheters 110 and 130). Balloon electrode tip 120 includes an inflatable balloon body 122 having an exterior surface 124 on which is disposed a pair of bipolar electrodes 156a and 156b. Balloon body 122 can be made of compliant or non-compliant material. Balloon body 122 can be inflated with a fluid (e.g., gas or liquid), and in some embodiments, balloon body is inflated with conductive fluid (e.g., saline) supplied from a fluid source. Inflation of balloon body 122 can be achieved by dispensing fluid into the interior chamber of balloon body 122 from one or more fluid outlet openings provided in either outer catheter 110 or inner catheter 130. In the embodiment shown in FIGS. 1 and 2, a plurality of fluid outlet openings 136 are provided in distal end portion 134 of inner catheter 130. Inner catheter 130 can have a lumen communicating with openings 136. The lumen forms a fluid channel for supplying fluid from a fluid source at a proximal end of inner catheter 130 to fluid outlet openings 136.

In embodiments where balloon body 122 is attached to outer catheter 110, fluid can be supplied into balloon body 122 via a fluid supply lumen in outer catheter 110. Fluid supply from outer catheter 110 (not shown) can be an alternative to or in addition to dispensing fluid from inner catheter 130 via openings 136. For example, outer catheter 110 can include a lumen that communicates with the interior chamber of balloon body 122 for filling balloon body 122 with fluid supplied from the lumen.

Balloon body 122 is provided with a plurality of weeping holes 126 which expel a portion of the fluid inflating balloon body 122. In some embodiments as described above, weeping holes 126 can be configured as valves that remain closed when balloon body 122 is deflated but which are opened when balloon body 122 is inflated to a given minimum inflation amount and/or internal pressure.

Figure 3B:
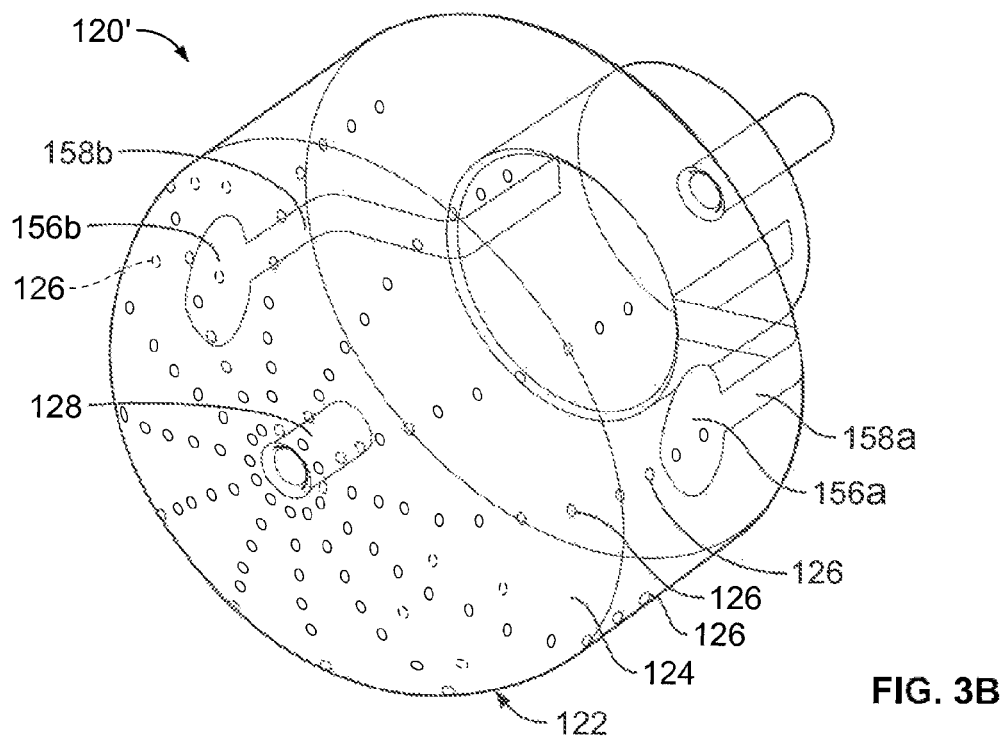
FIG. 3B illustrates a perspective view of the balloon electrode tip of FIG. 1 with electrodes disposed on a side of the balloon according to an embodiment presented herein.

Electrodes 156a and 156b can be placed anywhere on exterior surface 124 of balloon body 122. In the embodiments shown in FIGS. 1, 2 and 3A, electrodes 156a and 156b are disposed on the distal end of balloon body 122 (e.g., at hemispherical portion 164). Such electrode placement may be desirable for therapies requiring clearing of clogged vessels, whereby the electrodes at the distal end can be used to ablate the clogging tissue. For therapies requiring sealing of vessels or removal of tissue at sidewalls of a body lumen, it may be desirable to position electrodes 156a and 156b at a side of balloon body 122 (e.g., at cylindrical portion 162a), such as illustrated in an embodiment of a balloon electrode tip 120' shown in FIG. 3B. As shown in the embodiments of FIGS. 3A and 3B, weeping holes 126 are located in balloon body 122 in a region extending between the electrodes 156a and 156b. When conductive fluid is used to inflate balloon body 122 and weeps from holes 126, the wept conductive fluid exists in the region extending between the electrodes 156a and 156b and provides an electrical pathway adjoining electrodes 156a and 156b. In this manner, the placement of weeping holes 126 is determined in relation to the placement of electrodes 156a and 156b to ensure that fluid exiting the weeping holes 126 is provided to the electrodes to fluidly connect them together.

In the embodiment shown in FIGS. 1, 2, 3A and 3B, bipolar electrodes 156a and 156b are formed of conductive ink and include respective exposed, conductive electrode portions (at 156a and 156b) and respective lead portions 158a and 158b, whose exterior surfaces have been covered by an insulative material 155. Electrode lead portions 158a and 158b (and insulative material 155) extend proximally from the exposed electrode portions to a proximal portion 166 of balloon body 122 (see FIG. 3A). At proximal portion 166 of balloon body 122, electrode lead portions 158a and 158b meet catheter lead wires 118a and 118b (shown in phantom in FIGS. 1 and 2) at distal end portion 114 of outer catheter 110. Catheter lead wires 118a and 118b are connected to a power source (not shown) at the proximal end portion of outer catheter 110.

In some embodiments, a rigid ring 140 can be mounted on the exterior of a cylindrical portion 166a (see FIG. 3A) of proximal portion 166 over electrode lead portions 158a and 158b. As shown in FIGS. 1 and 2, the catheter lead wires 118a and 118b can extend onto the interior surface of ring 140 facing the cylindrical portion 166a to meet electrode lead portions 158a and 158b at a solder site 159, and ring 140 can serve as a substrate for soldering of electrode lead portions 158a and 158b to the catheter lead wires 118a and 118b at solder site 159. In the embodiment of FIGS. 1 and 2, ring 140 is secured within lumen 116 of outer catheter 110 (e.g., by an interference fit, adhesive, a bayonet locking mechanism, and/or other known attachment methods), thereby attaching proximal portion 166 of balloon body 122 to distal end portion 114 of outer catheter 110. Other methods as known in the art can also be employed for attaching proximal portion 166 of the balloon body to the outer catheter 110.

A distal portion of balloon body 120 can be attached to distal end portion 134 of inner catheter 130. As shown in FIG. 3A, balloon body 122 can include a distal portion 162 having a hemispherical portion 164 extending proximally to a cylindrical portion 162a. Hemispherical portion 164 includes an attachment portion 128 at a distal end 129b of balloon body 122. Attachment portion 128 attaches to distal end portion 134 of inner catheter 130. In some embodiments, attachment portion 128 is a rigid ring which can be secured to the outside of inner catheter (as shown in FIGS. 1 and 2) or secured within a lumen of inner catheter 130. The attachment between attachment portion 128 and inner catheter 130 can be achieved by an interference fit, adhesive, a bayonet locking mechanism, and/or other known attachment methods. Other methods as known in the art can also be employed for attaching of balloon body 122 to inner catheter 130 at distal end 129b of balloon body 122.

At a proximal end 129a of balloon body 122 (extending proximally from cylindrical portion 166a) is a cylindrical portion which forms a throat 123 of balloon body 122. Throat 123 has a proximal opening 123a for receiving inner catheter 130 into the interior chamber of balloon body 122. Throat 123 can have a diameter corresponding to either the outer diameter of inner catheter 130. Inner catheter 130 and throat 123 can have a fluid-tight sealing engagement, thereby permitting fluid dispensed from outlet openings 136 to fill the interior chamber of balloon body 122 and inflate balloon body 122.

When balloon body 122 is inflated, cylindrical portion 162a of distal portion 162 can abut against the distal end of outer catheter 110 as shown in FIG. 1. In some embodiments, distal end portion 114 of outer catheter 110 can be made of softer durometer material than the proximal end portion of outer catheter 110, to help prevent distal end portion 114 from compromising the elasticity of balloon body 122 (if made of compliant material), and/or to prevent piercing balloon body 122 once inflated.

In some embodiments, as shown in FIGS. 3A and 3B, balloon body 122 has a double diameter, in which distal portion 162 of balloon body 122 has one diameter and proximal portion 166 has another diameter. In the embodiments of FIGS. 3A and 3B, cylindrical portion 166a extending proximally from cylindrical portion 162a has a diameter that is less than that of cylindrical portion 162a in an inflated configuration. In some embodiments, balloon body 122 is attached to outer catheter 110 via ring 140, such as described above with reference to FIGS. 1 and 2. In such embodiments, the diameter of proximal cylindrical portion 166a can correspond with the diameter of ring 140 and likewise the inner diameter of lumen 116 which receives ring 140. Thus, cylindrical portion 166a can serve as a site where balloon body 122 is attached to outer catheter 110. Cylindrical portion 166a can also serve as a supporting base for distal cylindrical portion 162a to provide stability to distal portion 162 of balloon body 122. Enhancing the stability of distal portion 162 can help ensure that the exposed electrode portions of electrodes 156a and 156b on distal portion 162 can be steadily placed in contact with target tissue. In the embodiments of FIGS. 3A and 3B, distal portion 162 has a larger diameter than proximal portion 166 in an inflated configuration. In other embodiments, a double diameter balloon body can be provided in which distal portion 162 has a smaller diameter than proximal portion 166 in an inflated configuration.

Figure 4:
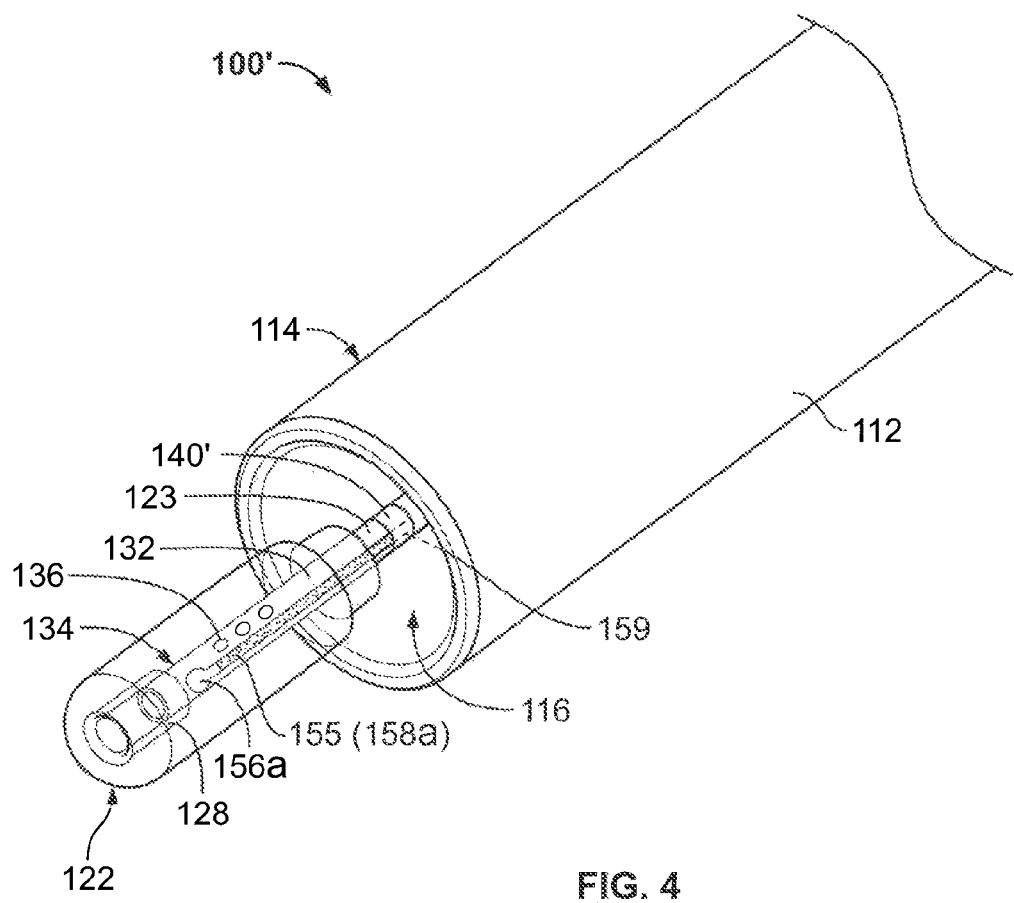
FIG. 4 illustrates a perspective view of a catheter assembly having a balloon electrode tip in a deflated configuration according to an embodiment presented herein.

FIG. 4 illustrates a catheter assembly 100' according to an embodiment presented herein. Catheter assembly 100' is a variation of catheter assembly 100 and differs in that balloon body 122 is not attached to outer catheter 110. In FIG. 4, elements with similar or identical function and configuration as those previously described for catheter assembly 100 are denoted with identical reference numbers, and therefore detailed explanation of such elements may be omitted or abbreviated. In the embodiment of FIG. 4 (showing balloon body 122 in its deflated configuration), balloon body 122 is attached to inner catheter 130 at attachment portion 128 (at distal end 129b, see FIG. 3A) and at throat 123 (at proximal end 129a, see FIG. 3A). A rigid ring 140' is provided around the exterior of throat 123 and serves as a soldering substrate for electrically connecting electrode lead portions 158a and 158b with catheter lead wires 118a and 118b at solder site 159 (catheter lead wires not shown in the view of FIG. 4; see, e.g., catheter lead wires 118a and 118b shown the embodiment of FIGS. 1 and 2). In the embodiment of FIG. 4, ring 140' crimps throat 123 onto the outside of inner catheter 130, and provides a fluid-tight seal between throat 123 of balloon body 122 and distal end portion 134 of inner catheter 130. Other methods as known in the art can also be employed for attaching of balloon body 122 to inner catheter 130 at throat 123.

In any of the embodiments described herein, inner catheter 130 can be slidably disposed within lumen 116 of outer catheter 110. In the embodiment of FIGS. 1 and 2, at least a portion of distal end portion 134 of inner catheter can be retracted inside lumen 116. In some embodiments, distal end portion 134 of inner catheter can retract a majority of deflated balloon body 122 inside lumen 116, which can provide protection to balloon electrode tip (e.g., tip 120 or 120' or other electrode tip embodiments described herein) until deployment at the surgical site. In comparison with catheter assembly 100, because balloon body 122 is not attached to outer catheter 110 in the embodiment of FIG. 4, distal end 134 of inner catheter 130 can retract the entirety of balloon body 122 inside lumen 116 of outer catheter 110.

The inflation amount and internal pressure of balloon body 122 can be varied to control the fluid flow rate of fluid from weeping holes 126 and to assist in achieving desired electrode contact on tissue surfaces. Moreover, the inflation amount and internal pressure of balloon body 122 can be varied to control the distance between bipolar electrodes 156a and 156b if the balloon body is made of compliant material. The inflation amount and internal pressure can be controlled by adjusting the amount of fluid dispensed into the internal chamber of balloon body 122 (via outlet openings 136) (i.e., the inflation amount) and/or by manipulating the position of distal end portion 134 of inner catheter 130 relative to distal end portion 114 of outer catheter 110. Adjustment of the inflation amount can be independent of or in conjunction with the manipulation of the relative position of the distal end portions of the inner and outer catheters.

As an illustration, in the embodiments of FIGS. 1, 2 and 4, when balloon body 122 is inflated, proximal movement of inner catheter distal end portion 134 relative to outer catheter distal end portion 114 can pinch balloon distal portion 162 against outer catheter distal end portion 114. This pinching action can cause a portion of balloon body 122 to collapse into outer catheter lumen 116, forcing fluid in the interior chamber of balloon body 122 into the remaining portion of balloon body 122 outside of lumen 116. The additional fluid increases the internal pressure and can increase the flow rate of fluid from weeping holes 126. For electrode positioning at the distal end of the balloon body such as in the embodiment of FIG. 3A, proximal movement of inner catheter 130 also pulls distal end 129b of balloon body 122 proximally (via their attachment at distal attachment portion 128), which causes electrodes 156a and 156b to be pushed distally inward closer together. For embodiments where proximal portion 166 of balloon body 122 is attached to outer catheter distal end portion 114 (see FIGS. 1 and 2), distal movement of inner catheter distal end portion 134 can elongate balloon body 122, which can cause electrodes 156a and 156b to be pushed away from each other, increasing their separation distance. The extent of balloon elongation can change the shape of a complaint balloon body so that electrodes 156a and 156b initially disposed at the distal end of the balloon body are moved to a side of the elongated balloon body. Additional fluid can be dispensed from inner catheter outlet openings 136 to cause further expansion of the remaining portion of balloon body 122 to change the fluid flow rate and/or the distance between electrodes 156a and 156b. As should be apparent, manipulation of balloon shape (via inflation amount and/or relative movement of the inner and outer catheters) may achieve a different result for different electrode positioning. For example, for electrodes on a side of the balloon body such as in the embodiment of FIG. 3B, the remaining portion of balloon body 122 (not collapsed in outer catheter 110) can expand under the increased pressure if balloon body is compliant. This can cause electrodes 156a and 156b to move apart despite distal end 129b of balloon body 122 being pulled proximally by proximal movement of inner catheter 130.

Weeping holes 126 can be configured to close when the balloon body is deflated and open when the balloon body 122 is inflated to a given minimum inflation amount and/or internal pressure. Increasing the inflation amount and/or internal pressure (beyond the minimum which opens holes 126) can increase the flow rate of fluid from holes 126, which may be desired to control the temperature at the treatment site. The flow rate of the electrically conductive fluid can affect the thermal characteristics of the tissue. For RF applications for example, when the fluid is electrically conductive fluid, the fluid can act as a heat sink, absorbing and carrying away excess or undesirable thermal energy resulting from electrically energizing electrodes 156a and 156b. The electrically conductive fluid can also provide electrical dispersion by distributing the applied current over a larger surface area, thereby limiting the potential for undesirable thermal concentration. An uncontrolled or abundant flow rate can provide too much electrical dispersion and cooling at the electrode/tissue interface. On the other hand, a flow rate that is too low could lead to excessive heat and arcing.

Moreover, the electrically conductive fluid can be used to help maintain temperatures within ranges conducive to coagulation of tissue (e.g., temperatures hot enough to denature the collagen and most soft tissue and bone, however not so hot that tissue is damaged to such an extent that it cannot be easily absorbed back into the body during a healing process) as opposed to charred, desiccated tissue. Collagen shrinkage, which causes coagulation, is a function of time and temperature. At 100° C., coagulation occurs substantially instantaneously, and at higher temperatures there will also be coagulation. Coagulation can begin at temperatures lower than 100° C., but the coagulation may occur more gradually. Without fluid (e.g., saline) present at the tissue being treated, temperatures can quickly rise above 100° C., and at such higher temperatures there is a greater likelihood of tissue sticking and charring. As one of skill in the art would appreciate, the time and temperature applied can be varied to suit a particular use. An RF power system can be controlled by suitable software to obtain desired power delivery characteristics. For example, in some embodiments, a control device or custom generator can be configured to allow the user to select a "pulse" mode of the RF power whereby the RF power to the balloon electrode tip is repeatedly turned on and off. Pulsed RF power may help effectively treat thick tissues as would be would be recognized by one of skill in the art. Moreover, in some embodiments, fluid flow rates from weeping holes 126 can be controlled based on the applied RF power to maintain temperatures at the treatment site within a desired range.

In embodiments described herein, saline has been provided as the exemplary electrically conductive fluid for filling balloon body 122 and expelling through weeping holes 126; however other electrically conductive fluids may be used alternatively or additionally, consistent with the embodiments presented herein. The fluid for filling balloon body 122 and expelling through weeping holes 126 may also comprise an electrically non-conductive fluid (e.g., deionized water and lactated ringers). The use of a non-conductive fluid still provides certain advantages over the use of a dry electrode including, for example, reduced occurrence of tissue sticking to the electrodes of the tip assemblies disclosed herein, and cooling of the electrodes and/or tissue.

In some embodiments, balloon electrode tip 120 (or 120') is provided with an inner balloon body (disposed inside the interior chamber of balloon body 122). An inner balloon body can provide balloon electrode tip 120 with a double-wall construction that is more resistant to displacement. The inner balloon body can serve as a support for electrode tip 120 to enhance the stability of balloon body 122 and help ensure that the exposed electrode portions of electrodes 156a and 156b on distal portion 162 can be steadily placed in contact with target tissue. The outer balloon body 122 can be adjustably inflated with fluid to vary its shape or internal pressure to control fluid flow rate from weeping holes 126, vary the distance between electrodes and/or achieve desired electrode contact on tissue surfaces. In some embodiments, the inner balloon body can always be filled with fluid once deployed (without adjustment).

An exemplary embodiment of a catheter assembly 200 having a double-wall construction formed by inner and outer balloons will now be described with reference to FIGS. 5-7. In these figures, elements with similar or identical function and configuration as those previously described for catheter assembly 100 are denoted with identical reference numbers, and detailed explanation of such elements may be omitted or abbreviated in the description that follows.

Catheter assembly 200 includes a double-walled balloon electrode tip 220 having an outer balloon body 222 and an inner balloon body 272. Outer balloon body 222 has an exterior surface 224 (on which one or more electrodes are disposed, not shown) and an interior chamber 222a within which is disposed inner balloon body 272. Inner balloon body 272 has an interior chamber 272a. The distal end of inner balloon body 272 is attached to distal end portion 134 of inner catheter 130 at an attachment portion 278a. The proximal end of inner balloon body 272 has a throat 273 with a proximal opening 273a for receiving distal end portion 134 of inner catheter 130 into interior chamber 272a. Throat 273 can have a diameter corresponding to the outer diameter of inner catheter 130. Inner catheter 130 and throat 273 can have a fluid-tight sealing engagement at attachment portion 278b (see FIG. 6), thereby permitting fluid dispensed from outlets in inner catheter 130 (such as outlet openings 136, see FIGS. 1 and 2) to fill interior chamber 272a of inner balloon body 272 and inflate inner balloon body 272. The distal end of outer balloon body 222 is also attached to distal end portion 134 of inner catheter 130 at an attachment portion 228 (similar to earlier-described attachment portion 128 of balloon body 122). Outer balloon attachment portion 228 is located distally from inner balloon attachment portion 278a. The proximal end of outer balloon body 222 is attached to distal end portion of 114 of outer catheter 110 (similar to earlier-described balloon body 122 of catheter assembly 100). In some embodiments, inner balloon body 272 and outer balloon body 222 are independently inflatable. Fluid can be dispensed from outlets in inner catheter 130 (such as outlet openings 136, see FIGS. 1 and 2) into chamber 222a of outer balloon body 222. Alternatively, fluid can be dispensed into chamber 222a of outer balloon body 222 from outlets provided in outer catheter 110. Alternatively, fluid can be dispensed into chamber 222a of outer balloon body 222 from fluid inflating chamber 272a of inner balloon body (e.g., via fluid outlet holes provided in inner balloon body 272).

A ring (such as ring 140) can be used to attach outer balloon body 222 to outer catheter 110, and a ring (such as ring 140') can be used to attach throat 273 of inner balloon catheter 272 to inner catheter 130. The attachment configurations illustrated in the embodiment of FIGS. 5-7 are exemplary only, and it should be understood that other methods as known in the art can also be employed for attaching of the inner and outer balloon bodies 272 and 222 to the inner and outer catheters 130 and 110. In some embodiments, outer balloon body 222 can have its proximal end attached to inner catheter 130 instead of being attached to outer catheter 110 (similar to earlier-described balloon body 122 of catheter assembly 100').

Figure 5:
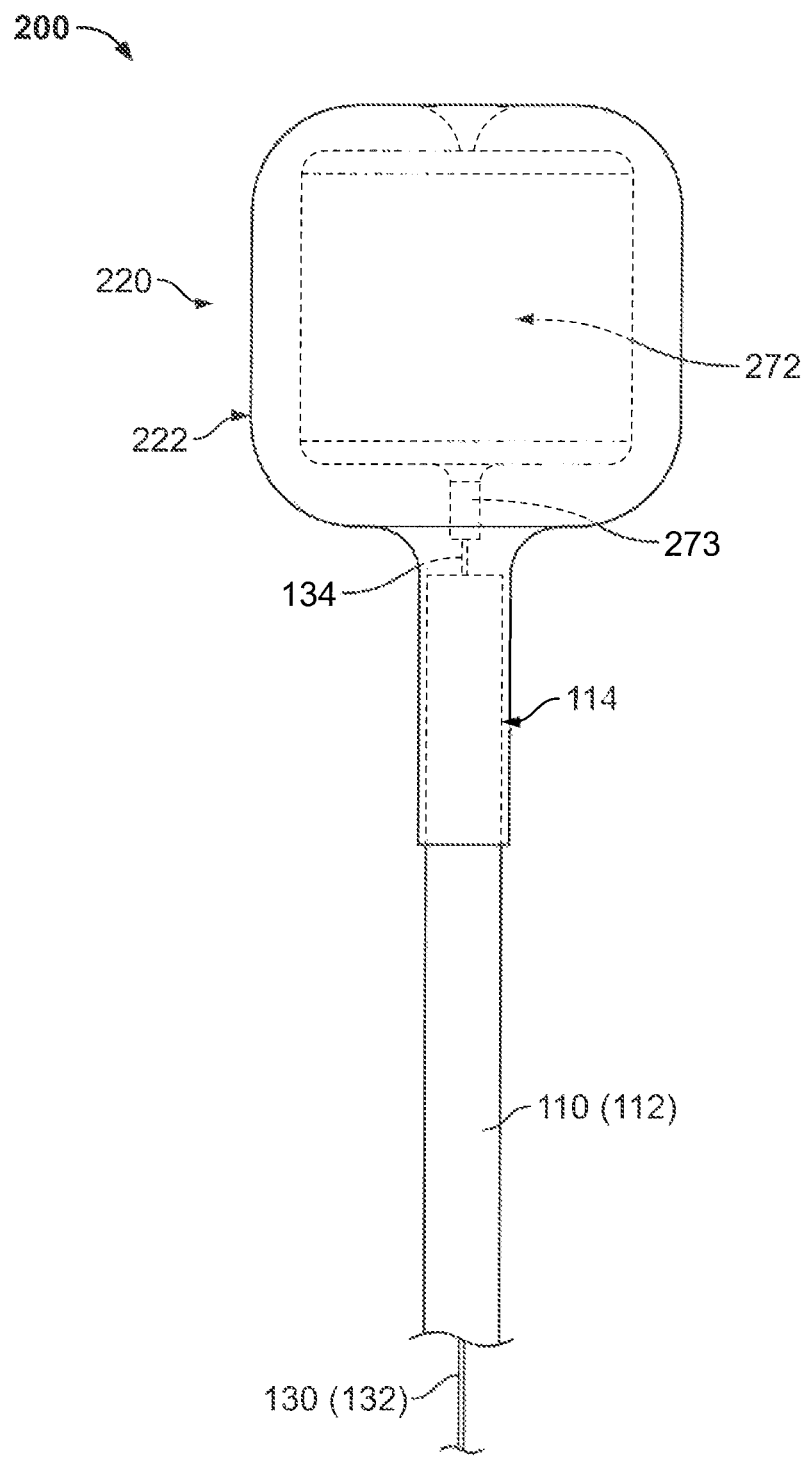
FIG. 5 illustrates a side view of a catheter assembly having a balloon electrode tip in an inflated configuration according to an embodiment presented herein.
Figure 6:
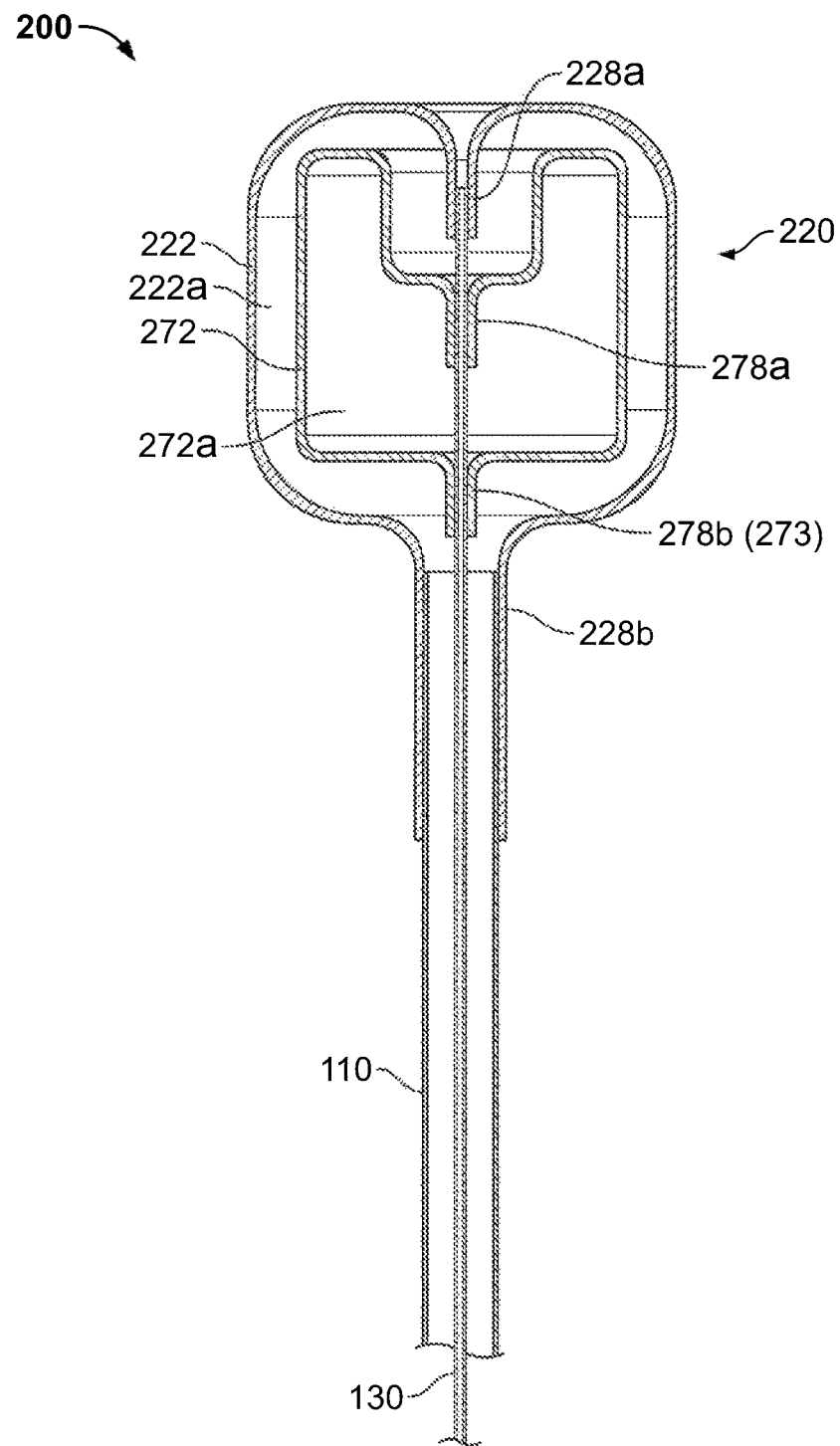
FIG. 6 illustrates a longitudinal cross-sectional view of the catheter assembly of FIG. 5.
Figure 7:
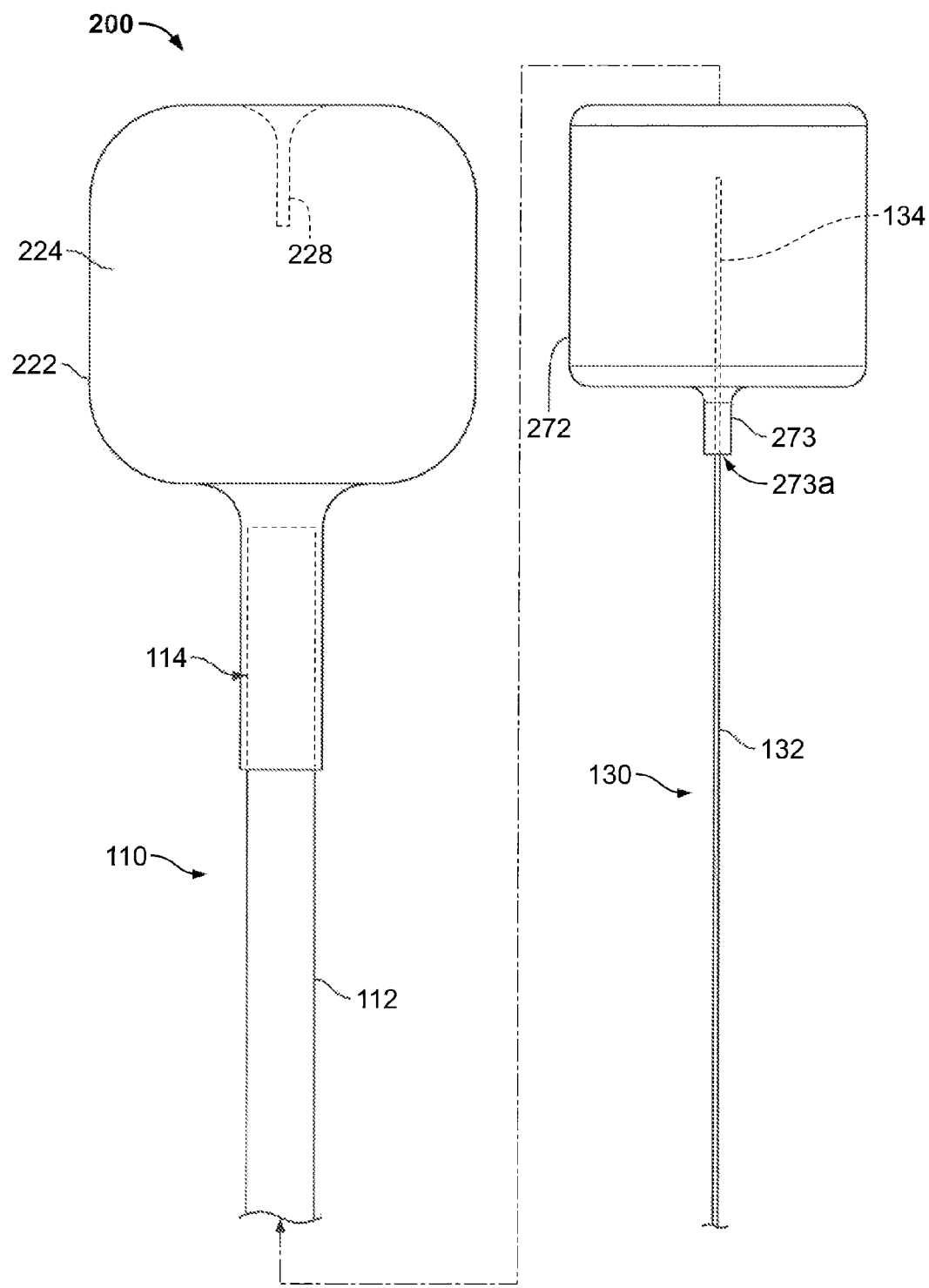
FIG. 7 illustrates an exploded side view of the catheter assembly of FIG. 5.

Electrode(s), weeping holes and fluid outlets in the balloon bodies and catheters have been omitted from illustration in the views of FIGS. 5-7; however, it should be understood that catheter assembly 200 can be provided with fluid outlet opening(s) (such as outlet openings 136) in inner catheter 130 for dispensing fluid to inflate inner balloon body 272, and fluid outlet opening(s) in inner or outer catheters 130 and 110 for inflating outer balloon body 222, as earlier described. It should be understood that catheter assembly 200 can also be provided with one or more electrodes, including in some embodiments a bipolar electrode pair (such as electrodes 156a and 156b), and weeping holes (such as holes 126) configured to provide fluid to the bipolar electrode pair, as earlier described. It should also be understood that any of the features of a balloon electrode tip described herein (including but not limited to the features described with reference to a balloon electrode tip having a single balloon body, such as the features described with reference to catheter assemblies 100 and 100' of FIGS. 1, 2, 3A, 3B, and 4), are applicable to a double-wall balloon electrode tip having two balloon bodies (e.g., balloon electrode tip 220 of catheter assembly 200). Therefore, further detailed description of such features with respect to embodiments of a double-wall balloon electrode tip is omitted for brevity.

Figure 8A:
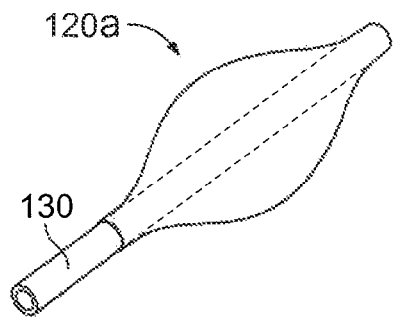
FIGS. 8A-8C illustrate perspective views of exemplary balloon shapes of balloon electrode tips according to embodiments presented herein.
Figure 8B:
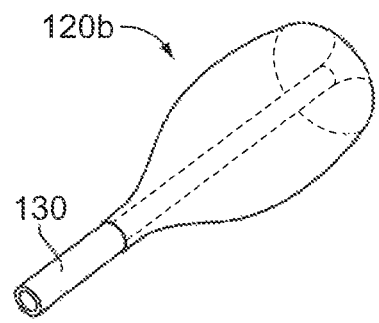
Figure 8C:
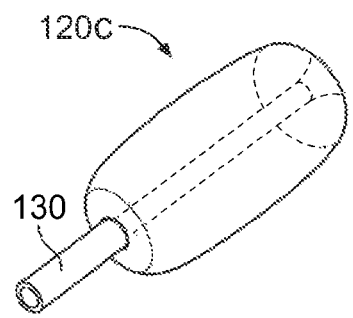

The foregoing description of the specific embodiments of the devices and methods described with reference to the Figures will so fully reveal the general nature of the invention that others can, by applying knowledge within the skill of the art, readily modify and/or adapt for various applications such specific embodiments, without undue experimentation, without departing from the general concept of the present invention. For example, as earlier noted, the balloon electrode can have a balloon body of any configuration or shape (e.g., tubular, spherical, etc.) and can be various sizes, allowing the balloon to be designed for a myriad of therapies. FIGS. 8A-8C illustrate perspective views of exemplary balloon shapes of balloon electrode tips 120a, 120b, and 120c according to embodiments presented herein. In these illustrations, attachment of balloon electrode tips 120a, 120b, and 120c to inner catheter 130 is also shown. Balloon electrode tip 120a has a balloon body with an elliptical central portion tapering to opposite cylindrical end portions that attach to inner catheter 130 and have the same contour as inner catheter 130. Balloon electrode tip 120b is similar to tip 120a but has a blunted distal end portion where the balloon body has been folded inward to attach to inner catheter 130 (comparable to the attachment configurations of balloon bodies 122 and 222 to inner catheter 130 in the embodiments of FIGS. 1, 2, 4 and 5-7). Balloon electrode tip 120c has a cylindrical balloon body having blunted proximal and distal end portions where the balloon body attaches at proximal and distal ends thereof to the inner catheter 130.

Figure 9A:
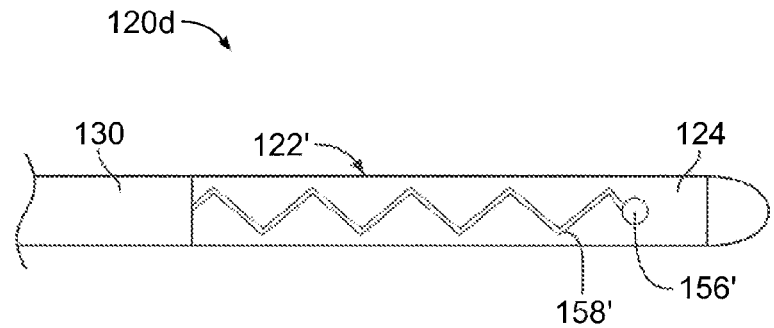
FIG. 9A illustrates a side view of a catheter assembly having a balloon electrode tip in a deflated configuration according to an embodiment presented herein.
Figure 9B:
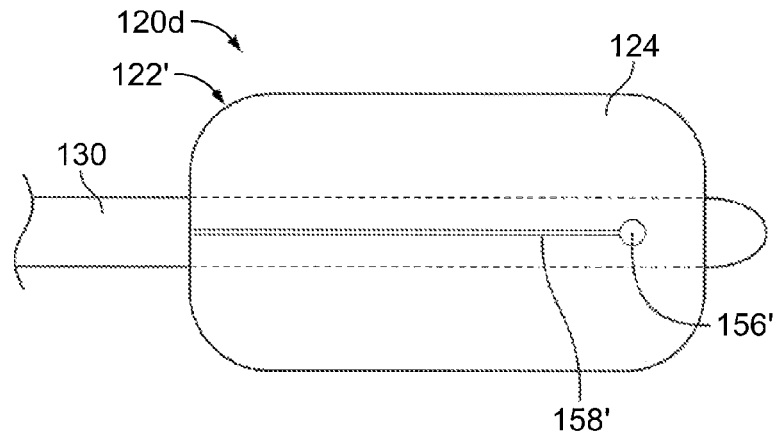
FIG. 9B illustrates a side view of the catheter assembly of FIG. 9A having the balloon electrode tip in an inflated configuration according to an embodiment presented herein.

Also, in any of the embodiments disclosed herein, a biocompatible conductive wire can used for the one or more balloon electrodes in place of a conductive ink electrode, and vice versa. Thus, conductive ink electrodes 156a and 156b can be replaced with wire electrodes. In some embodiments, the exposed electrode portions of electrodes 156a and 156b can be formed of conductive ink, and their lead portions 158a and 158b can be formed of wire leads. In embodiments using wire electrodes on the exterior surface of the balloon body, the wire electrode should be configured to extend with balloon expansion. An exemplary configuration of a wire electrode 156' having a wire lead portion 158' is illustrated in FIGS. 9A and 9B. As shown in FIG. 9A, a balloon electrode tip 120d has wire electrode 156' provided on exterior surface 124 of a deflated balloon body 122'. Wire lead portion 158' has a zigzag configuration along the length of deflated balloon body 122'. As shown in FIG. 9B, inflation of balloon body 122' causes wire lead portion 158' to extend longitudinally and straighten. Thus, the prior zigzag configuration of wire lead portion 158' is straightened with balloon inflation.

Figure 10:
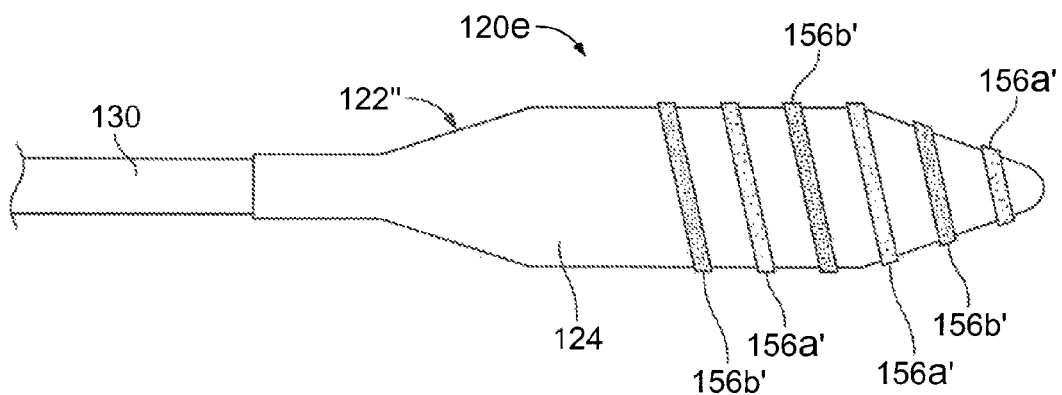
FIG. 10 illustrates a side view of a catheter assembly having a balloon electrode tip in an inflated configuration according to an embodiment presented herein.

Also, in any of the embodiments disclosed herein, the one or more balloon electrodes can be placed anywhere on the exterior surface of the balloon body. As described above with reference to FIGS. 3A and 3b, in some embodiments, a pair of bipolar electrodes (e.g., electrodes 156a and 156b) can be being disposed on the exterior surface the balloon body (e.g., balloon body 122) at one of the side and the distal end of the balloon body. Other electrode placements can also be employed. For example, one electrode of a bipolar electrode pair can be placed at the distal end of the balloon body and the other electrode can be placed at the side. Another exemplary configuration of an electrode placement is illustrated in FIG. 10. As shown in FIG. 10, a balloon electrode tip 120e includes a pair of bipolar electrodes 156a' and 156b' provided on exterior surface 124 of a balloon body 122". Balloon body 122" has a cylindrical central portion extending to a conically-shaped distal end portion. Bipolar electrodes 156a' and 156b' extend helically around these cylindrical and conical portions of balloon body 122". With such a configuration, energization of helical electrodes 156a' and 156b provides a greater tissue treatment area proximally (at the cylindrical portion) than distally (at the conical portion). The conical portion can provide focused energy over a smaller tissue treatment area, which may be particular useful for blunt dissection of tissue. The cylindrical portion, which can target a greater tissue treatment area, may be particularly useful for tissue sealing.

In any of these embodiments of the exemplary balloon electrode tips 120a-e illustrated in FIGS. 8A-8C, 9A-9B, and 10, a catheter assembly can constitute the balloon electrode tip and the inner catheter 130. In some embodiments, the catheter assembly can further include outer catheter 110 (see, e.g., FIGS. 1, 2, and 5-7). As earlier described, outer catheter 110 can be configured to house inner catheter 130 and also house all or part of the collapsed balloon electrode tip. At the target surgical site, inner catheter distal end portion 134 can be extended from outer catheter distal end portion 114, and the balloon electrode tip then deployed. As should be apparent, in any of these embodiments, balloon electrode tips 120a-e can be modified to also attach to outer catheter 110 (comparable to the attachment configurations of balloon body 122 and balloon body 222 in the embodiments of FIGS. 1, 2 and 5-7). As also should be apparent, in any of these embodiments, balloon electrode tips 120a-e can be modified to have a double balloon configuration, i.e., be provided with an inner balloon body (such as inner balloon body 272) disposed within the chambers of the balloon bodies illustrated in FIGS. 8A-8C, 9A-9B, and 10.

Also, for example, in some embodiments the bipolar balloon electrode tips described herein can be used as a selectably monopolar tip, switchable between a bipolar mode and a monopolar mode. In the monopolar mode, at least one of the electrodes 156a and 156b is connected to a power generator so as to deliver energy as a monopolar (active) electrode, and there is no return electrode on the device (rather, a ground pad on the patient may be used as known in the art). A monopolar electrode system can be particularly suitable for ablating tissue. In some embodiments, the monopolar electrode may be supplied with RF energy (including pulsed RF energy), ultrasonic energy, or any other suitable energy for ablating tissue.

Therefore, it should be apparent that adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The breadth and scope of the present invention should not be limited by any of the above-described exemplary embodiments, but should be defined only in accordance with the following claims and their equivalents.

What is claimed is:
1. An electrosurgical balloon, comprising:
   an inflatable balloon body having a proximal end and a distal end and defining a circumference, wherein the balloon body is formed of a nonconductive substrate material;
   a pair of bipolar electrodes disposed on an opposite sides of an exterior surface of the inflatable balloon body, the pair of electrodes including a first electrode and a second electrode in a bipolar electrode configuration, each the first electrode and the second electrode extending partially around the circumference of the inflatable balloon body; and
   at least one fluid outlet hole in the balloon body configured to provide a conductive fluid from a fluid source to the pair of bipolar electrodes.

2. The electrosurgical balloon of claim 1, wherein the balloon body is configured to be adjustably inflated with the conductive fluid from the fluid source.

3. The electrosurgical balloon of claim 2, wherein adjustment of an amount of inflation of the balloon body is configured to adjust a separation distance between the first and second electrodes.

* * * * *